United States Patent [19]
Ujvari et al.

[11] 4,022,896
[45] May 10, 1977

[54] XANTHENE AND THIOXANTHENE COMPOSITIONS AND METHOD OF TREATING

[75] Inventors: Georg Ujvari, Nykobing S; Peter Bregnedal Hansen, Horsholm, both of Denmark

[73] Assignee: Kefalas A/S, Copenhagen-Valby, Denmark

[22] Filed: Mar. 1, 1976

[21] Appl. No.: 662,331

Related U.S. Application Data

[62] Division of Ser. No. 525,967, Nov. 21, 1974, Pat. No. 3,951,961.

[30] Foreign Application Priority Data

Nov. 30, 1973 United Kingdom ............ 55759/73

[52] U.S. Cl. .................... 424/250; 260/240 TC; 424/275
[51] Int. Cl.$^2$ ............. A61K 31/395; A61K 31/445
[58] Field of Search ................. 424/250, 267, 275; 260/240 TC, 250, 267

[56] References Cited
UNITED STATES PATENTS

| | | | |
|---|---|---|---|
| 2,951,082 | 8/1960 | Sprague et al. ................. | 260/328 |
| 3,192,204 | 6/1965 | Craig et al. .................... | 260/240 |
| 3,282,930 | 11/1966 | Craig et al. ................... | 260/268 TR |
| 3,310,553 | 3/1967 | Bloom et al. ................. | 260/240 TC |
| 3,374,231 | 3/1968 | Cusic et al. .................. | 260/240 TC |
| 3,681,346 | 8/1972 | Petersen et al. .............. | 260/240 TC |

*Primary Examiner*—Arthur P. Demers
*Attorney, Agent, or Firm*—Gordon W. Hueschen

[57] ABSTRACT

The present invention relates to novel xanthene and thioxanthene derivatives of the following general formula:

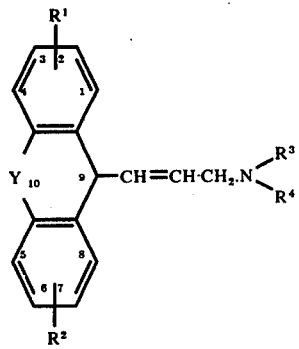

wherein

Y represents sulfur or oxygen, $R^1$ represents hydrogen, chlorine, trifluoromethyl or dimethylsulfamoyl, $R^2$ represents hydrogen or fluorine; and $R^3$ and $R^4$ each represents hydrogen or methyl, provided that $R^3$ and $R^4$ may not both represent hydrogen, or $R^3$ and $R^4$ taken together with the nitrogen atom form a piperazine or piperidine ring optionally substituted in the 4-position by a methyl group or a 2-hydroxyethyl group, if desired, esterified with an aliphatic carboxylic acid having from one to seventeen carbon atoms inclusive, as well as non-toxic acid addition salts thereof.

15 Claims, No Drawings

XANTHENE AND THIOXANTHENE COMPOSITIONS AND METHOD OF TREATING

This is a division of application Ser. No. 525,967, filed Nov. 21, 1974, and U.S. Pat. No. 3,961,961.

BRIEF SUMMARY OF THE INVENTION

It is an object of the present invention to provide compounds of Formula I, a method of making the same, a method for the alleviation, palliation, mitigation, or inhibition of the manifestations of certain physiologicalpsychlological abnormalies of animals therewith, and pharmaceutical compositions comprising such novel compounds as active ingredients. Other objects will be apparent to one skilled in the art and still other objects will become apparent hereinafter.

BACKGROUND OF THE INVENTION

For some years aminoalkylidene substituted thiaxanthenes having a substituent in position 2 of the phenyl rings have been found useful as tranquilizers and neuroleptics in the treatment of psychoses, and among them may be mentioned chlorprothixene (trans-9-(3-dimethylaminopropylidene)-2-chloro-thioxanthene), clopenthixol (9-[3(4-(2-hydroxyethyl)piperazinyl-(1))-propylidene]-2-chloro-thioxanthene) and flupenthixol (9-[3-(4-(2-hydroxyethyl)piperazinyl-(1))-propylidene ]-2-trifluoromethyl-thioxanthene.

A reliable method useful for the preparation of these thioxanthenes consists in the addition of an amine to a abnormalies of animals therewith, and pharmaceutical compositions comprising such novel compounds as active ingredients. Other objects will be apparent to one skilled in the art and still other objects will become apparent hereinafter.

For some years aminoalkylidene substituted thiaxanthenes having a substituent in position 2 of the phenyl rings have been found useful as tranquilizers and neuroleptics in the treatment of psychoses, and among them may be mentioned chlorprothixene (trans-9-(3-dimethylaminopropylidene)-2-chloro-thioxanthene), clopenthixol (9-[3(4-(2-hydroxyethyl) piperazinyl-(1))-propylidene]2-chloro-thioxanthene) and flupenthixol (9-[3-(4-(2-hydroxyethyl)piperazinyl-(1))-propylidene]-2-trifluoromethyl-thioxanthene. A reliable method useful for the preparation of these thioxanthenes consists in the addition of an amine to a 9-allylidene-thiaxanthene whereby aminopropylidenethioxanthenes are obtained in satisfactory yields when the reaction is carried out at elevated temperatures. The reaction may be illustrated by the following reaction scheme:

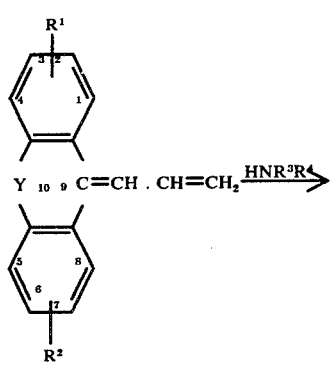

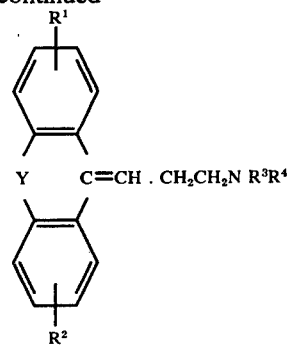

It has now surprisingly been found according to the method of the present invention that when a compound of Formula II wherein Y, $R^1$ and $R^2$ are as previously defined is treated with an amine of the formula:

about room temperature and with exclusion of light there is obtained a compound of Formula I which may be isolated as the free base or in the form of a non-toxic acid addition salt, and in the event where the compound of Formula I contains a free hydroxyl group, if desired, reacting with a reactive derivative of an aliphatic carboxylic acid having from 1–17 carbon atoms inclusive, and isolating the ester formed as the free base or a non-toxic acid addition salt thereof. The addition is preferably carried out in an inert solvent such as an alcohol, for example ethanol, and with excess of the amine of Formula III.

The starting compounds of Formula II are prepared by reacting a xanthene of thioxanthene of formula:

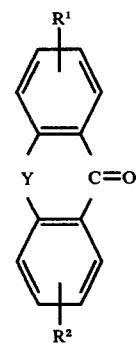

wherein Y, $R^1$ and $R^2$ are as previously defined, with allyl magnesium bromide, hydrolysing the Grignard complex formed, and dehydrating the xanthenol or thioxanthenol in wellknown manner, for example as described in U.S. Pat. No. 3,116,291.

Preferred compounds of this invention are those of Formula I in which Y is sulfur, $R^1$ is chlorine, trifluoromethyl or dimethylsulfamoyl at position 2, $R^2$ is hydrogen or fluorine at position 6 $R^3$ and $R^4$ together with the nitrogen atom form a 2-hydroxyethyl substituted piperazine ring optionally esterified with an aliphatic carboxylic acid residue with from 1–17 carbon atoms inclusive.

This invention also includes pharmaceutically acceptable salts of the bases of Formula I with non-toxic organic and inorganic acids. Such salts are easily prepared by methods known to the art. The base is reacted with either the calculated amount of organic or inorganic acid in an aqueous miscible solvent, such as acetone or ethanol, with isolation of the salt by concentration and cooling or an excess of the acid in aqueous immiscible solvent, such as ethyl ether or chloroform, with the desired salt separating directly. Exemplary of such organic salts are those with maleic, fumaric, benzoic, ascorbic, embonic, succinic, bis methylene-salicyclic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids as well as the 8-halotheophyllines, for example 8-bromotheophylline. Exemplary of such inorganic salts are those with hydrochloric, hydrobromic, sulfuric, sulfamic, phosphoric and nitric acids. Of course, these salts may also be prepared by the classical method of double decomposition of appropriate salts which is well known to the art.

The new compounds of Formula I may exist in the form of two geometric isomers. The individual isomers have the valuable pharmacodynamic effects in varying degrees. The single isomers and their isolation fall likewise within the scope of the present invention.

The compounds of Formula I and the non-toxic acid addition salts thereof may be administered both orally and parenterally, for example in the form of tablets, capsules, powders, syrups or solutions for injection.

When preparing esters of compounds of Formula I having a hydroxy group, i.e., when $R^3$ and $R^4$ taken together with the nitrogen atom form a piperazine or piperidine ring substituted in the 4-position with a 2-hydroxyethyl group, the reactive derivative of the aliphatic carboxylic acid in question is advantageously an acid halide or acid anhydride of the acid. As acids useful for this purpose may be mentioned acetic acid, propionic acid, butyric acid, valeric acid, enenthic acid, decanoic acid, hendecanoic acid and palmitic acid. Other acids may, however, be used equally well.

The following examples are given to illustrate the method and products of the present invention but, they are to be understood as exemplary only and are not to be construed as limiting.

EXAMPLE 1

2-Trifluoromethyl-6-fluoro-9-(3-(4-(2-hydroxyethyl)-piperazin-1-yl)1-propenyl)thioxanthene and its dihydrochloride.

The starting material, 2-trifluoromethyl-6-fluoro-9-allylidene thioxanthene, was prepared in the following way:

200 grams of 2-trifluoromethyl-6-fluoro-9-thioxanthone were added to a Grignard solution prepared from 160 grams of allylbromide and 192 grams of magnesium in 1 liter ether. The mixture was refluxed for 15 minutes, allowed to cool and poured into aqueous ammonium chloride solution. The ether phase was separated, extracted with 300 milliliters of water three times and the ether phase evaporated in vacuum. The residue was dissolved in 300 milliliters of benzene and 70 milliliters of acetic anhydride, 3 milliliters of acetylchloride and one drop of concentrated sulfuric acid were added. The mixture was heated an a steam bath at about 65 ° C until the dehydration sets in and then for a further 15 minutes. After cooling the mixture was poured onto crushed ice, made alkaline with sodium hydroxide, extracted with 1 liter of ether, washed 3 times with 100 milliliters of water, dried over anhydrous magnesium sulfate and evaporated in vacuum. Yield: 210 grams of 2-trifluoromethyl6-fluoro-9-allylidene thioxanthene as a yellow oil.

60 grams of 2-trifluoromethyl-6-fluoro-9-allylidene thioxanthene were dissolved in 200 milliliters of N-(2-hydroxyethyl)-piperazine and left standing at room temperature in the dark for 100 hours. The mixture was poured into 1 liter water and extracted with 1 liter ether. The ether phase was separated, washed three times with 200 milliliters of water and dried over anhydrous magnesium sulfate. After filtration the dihydrochloride was precipitated directly from the ether phase with an ether solution of dry hydrogen chloride. The ether was decanted and the dihydrochloride crystallized from 2propanol/acetone (1:1). After recrystallization from 99% ethanol/ether (1:1) it melts at 199°–202° C. Yield: 16.5 grams of the dihydrochloride of 2-trifluoromethyl-6-fluoro-9-(3-(4-(2-hydroxyethyl)piperazin-1-yl)1-propenyl)thioxanthene.

EXAMPLE 2

2-Trifluoromethyl-6-fluoro-9-(3-(4-methylpiperazine-1-yl)1-propenyl)thioxanthene and its dihydrochloride.

50 grams of 2-trifluoromethyl-6-fluoro-9-allylidene thioxanthene were mixed with 50 grams of N-methyl-piperazine and left standing in the dark at room temperature for 150 hours. The mixture was poured into 1 liter water and extracted with 1 liter ether, the ether phase washed 3 times with 200 milliliters of water, dried over anhydrous magnesium sulfate and filtered. The dihydrochloride was precipitated by adding ether saturated with dry hydrogen chloride and the ether phase decanted. 9 grammes of the dihydrochloride of 2-trifluoromethyl-6-fluoro-9-(3-(4-methylpiperazin-1-yl)$_1$-propenyl)thioxanthene crystallized from 99% ethanol/acetone (1:1) and melted at 268°–270° C.

EXAMPLE 3

2-Trifluoromethyl-6-fluoro-9-(3-dimethylamino1-propenyl) thioxanthene and its hydrochloride.

50 grams of 2-trifluoromethyl-6-fluoro-9-allylidene thioxanthene were dissolved in a 30% solution of dimethylamine in ethanol and left standing in the dark at room temperature for 150 hours. The mixture was worked up as described in Example 1 except that the hydrochloride of 2-trifluoromethyl-6-fluoro-9-(3-dimethylamino-1-propenyl) thioxanthene precipitated from ether crystallized from acetone/ether (1:1) and melted at 177°–180° C. Yield: 14 grams.

EXAMPLE 4

2-Trifluoromethyl-6-fluoro-9-(3-(4-(2-hydroxyethyl)-piperazine-1-yl)-1-propenyl) xanthene and its dioxalate.

The starting material, 2-trifluoromethyl-6-fluoro-9-(2allylidene xanthene, was prepared in the following way: 162 grams of 92% sodium ethanolate were dissolved in 750 milliliters of dimethylformamide and 260 grams of 3-fluorophenol, 530 grams of 2-chloro-5-trifluoromethylbenzonitrile, 25 grams of Adams Copper catalyst and 25 grams of cuprus iodide were dded. The mixture was heated to 150° C without reflux condenser, whereupon a reflux condenser was placed in a neck of the flask and heating was continued for 3 hours at 160° C. Dimethylformamide was distilled off in vacuum. The residue was suspended in water and extracted with chloroform, the chloroform-layer separated, washed with water, filtered and evaporated. The residue was dissolved in 1500 milliliters of 96% ethanol and 500 milliliters of water, whereupon 530 grams of potassium hydroxide were added in small portions and the mixture refluxed for 18 hours. 700 milliliters of concentrated hydrochloric acid were added dropwise and ethanol evaporated, whereupon the mixture was cooled and extracted with 2000 mililiteres of ether. The ether phase was separated, washed with water, dried over anhydrous magnesium sulfate and evaporated in vacuum. The residue consisted of 2-(3-fluorophenyloxy)-5-trifluoromethyl-benzoic acid as an oil. Yield: 700 grams.

700 grams of 2-(3-fluorophenyloxy)-5-trifluoromethylbenzoic acid were dissolved in 3,000 milliliters of concentrated sulfuric acid whereby the temperature rose to 60° C. The mixture was stirred at 45–50° C for one hour and then poured onto 10 liters of crushed ice. The precipitate was filtered off, suspended in 1,000 milliliters of acetone, made alkaline with concentrated aqueous ammonia and reprecipitated with ice and water to a volume of 10 liters. The precipitate was filtered, washed with water and dried in vacuum, whereupon it was recrystallized to yield 167 grams of 2-trifluoromethyl-6-fluoroxanthen-9-one which melts at 140°–142° C.

121 grams of allylbromide were added dropwise to 140 grams of magnesium turnings in 2000 milliliters of dry ether, whereupon the mixture was refluxed for 30 minutes. The ether phase was decanted and the magnesium turnings washed twice with 200 milliliters of dry ether. To the combined ether phases were added 164 grams of 2-trifluoromethyl-6-fluoro-xanthen-9-one and the mixture refluxed for 30 minutes. Then the mixture was poured into an aqueous ammonium chloride solution. The ether phase was separated and the etherphase washed three times with 500 milliliters of water, the etherphase dried over anhydrous magnesium sulfate and evaporated in vacuum. The residue consisted of 220 grams of 2-trifluoromethyl-6-fluoro-9-allyl xanthen-9-ol, which were dissolved in 250 milliliters of dry benzene, and 70 milliliters of acetic anhydride and 3 milliliters of acetylchloride were added. The mixture was heated gently to 60° C where the reaction began. After 10 minutes the mixture was poured onto crushed ice, 200 milliliters of concentrated sodium hydroxide were added, and the resulting mixture extracted with 1000 milliliters of ether, the ether phase separated, washed three times with 200 milliliters of water, dried over anhydrous magnesium sulfate and evaporated in vacuum, whereby 200 grams of 2-trifluoromethyl-6-fluoro-9- allylidene xanthene were obtained as a yellow oil.

50 grams of 2-trifluoromethyl-6-fluoro-9-allylidene xanthene were dissolved in 50 grams of N-(2-hydroxyethyl)piperazine and 50 milliliters of 99% ethanol and the mixture left standing in the dark at room temperature for 190 hours. The mixture was poured into 1,000 milliliters of water and extracted with 1,000 milliliters of ether, the ether phase separated, washed three times with 200 milliliters of water, dried over anhydrous magnesium sulfate and the dioxalate precipitated by adding a solution of oxalic acid in acetone. The ether phase was decanted and the precipitate recrystallized from acetone.

3.2 grams of the dioxalate of 2-trifluoromethyl-6-fluoro-9-(3-(4-(2-hydroxyethyl)piperazin-1-yl)-1-propenyl) xanthene was thus obtained as white crystals which melt at 220–222° C.

EXAMPLE 5

When Example 4 was carried out using 50 grams of 4-(2-hydroxyethyl) piperidine instead of N-(2-hydroxyethyl) piperazine 14 grams of the dioxalate of 2-trifluoromethyl-6-fluoro-9-(3-(4-(2-hydroxyethyl) piperidin1-yl)-1-propenyl xanthene were obtained as white crystals melting at 109°–111° C.

EXAMPLE 6

2-Chloro-9-(3-dimethylamino-1-propenyl)thioxanthene, its hydrochloride and is oxalate.

When Example 3 was carried out using 50 grams of 2-chloro9-allylidene thioxanthene instead of 50 grams of 2-trifluoromethyl-6-fluoro-9-(2-propenylidene)-thiaxanthene the hydrochloride of 2-chloro-9-(3-dimethylamino-2-propenyl)thiaxanthene was obtained as colourless crystals melting at 191°–193° C. Yield: 20 grams. The corresponding oxalate melts at 157°–160° C.

EXAMPLE 7

2-Chloro-9-(3-(4-(2-hydroxyethyl)piperazin-1-yl)-1-propenyl)thioxanthene and its dihydrochloride.

When Example 1 was carried out using 60 grammes of 2-chloro9-allylidene thioxanthene instead of 2-trifluoromethyl-6-fluoro-9-allylidene thioxanthene the hydrochloride of 2-chloro-9-(3-(4-(2-hydroxyethyl)-piperazin-1-yl)-1-propenyl) thioxanthene was obtained melting at 250°–260° C. Yield: 8 grams.

EXAMPLE 8

2-Trifluoromethyl-9-(3-(4-(2-hydroxyethyl)piperazin-1-yl)-1-propenyl)thioxanthene and its dihydrochloride.

When Example 1 was carried out using 60 grams of 2-trifluoromethyl-9-allylidene thioxanthene instead of 2-trifluoromethyl-6-fluoro-9-allylidene thioxanthene the dihydrochloride of 2-trifluoromethyl-9-(3-(4-(2-hydroxyethyl)piperazine-1-yl)-1-propenyl)thioxanthene was obtained as colourless crystals melting at 205°–209° C.

EXAMPLE 9

Other 1-propenyl substituted thioxanthenes and xanthenes.

In the same manner starting from the appropriated substituted 9-allylidene thioxanthene or xanthene were prepared:

2-Dimethylsulfamoyl-6-fluoro-9-(3-(4-(2-hydroxyethyl)-1-piperidyl)-1-propenyl)thioxanthene and its maleate.

2-Dimethylsulfamoyl-6-fluoro-9-(3-(4-methylpiperazinyl)-1-propenyl)thioxanthene and its dihydrochloride.

2-Trifluoromethyl-6-fluoro-9-(3-methylamino-1-propenyl) thioxanthene and its hydrochloride.

2-Trifluoromethyl-9-(3-dimethylamino-1-propenyl) thioxanthene and its hydrochloride.

4-Chloro-6-fluoro-9-(3-(4-(2-hydroxyethyl)-piperazin-1-yl)-1-propenyl)thioxanthene and its diacetate.

4-Trifluoromethyl-6-fluoro-9-(3-dimethylamino-1-propenyl) thioxanthene and its hydrochloride.

9-(3-(4-(2-hydroxyethyl)-piperazine-1-yl)-1-propenyl) thioxanthene and its dihydrochloride.

9-(3-dimethylamino-1-propenyl)thioxanthene and its hydrochloride.

EXAMPLE 10

2-Trifluoromethyl-6-fluoro-9-(3-(4-(2-hydroxyethyl)-piperidine)-1-propenyl)thiaxanthene and its sulphate.

When Example 1 was carried out using 4-(2-hydroxyethyl)-piperidine instead of N-(2-hydroxyethyl)-piperazine and using sulphuric acid instead of hydrogen chloride the sulphate of 2-trifluoromethyl-6-fluoro-9-(3-(4-(2-hydroxyethyl)-piperidine)1-propenyl)-thioxanthene was obtained as a white crystalline substance which melts unsharply about 100° C.

EXAMPLE 11

The palmitic acid ester of 2-trifluoromethyl-6-fluoro-9-(3-(4-(2-hydroxyethyl)-piperazin-1-yl)1-propenyl)thioxanthene.

9 grams of 2-trifluoromethyl-6-fluoro-9-(3-(4-(2-hydroxyethyl)piperazine-1-yl)-1-propenyl were dissolved in 50 milliliters of dry acetone and the solution cooled to zero degrees Centigrade. At this temperature were added 10 grams of palmitoyl chloride and the mixture was left standing in the dark while stirring for 18 hours at room temperature. An excess of dry hydrogen chloride in ether was added and the mixture evaporated in vacuum. Dry ether was added and the mixture filtered. The waxy precipitate was dried in a desiccator, pulverized and converted to the base by extracting with 200 milliliters of ether from a cold alkaline solution. The ether phase was shaken with 100 milliliters of 1N sodium hydroxide solution, dried over anhydrous magnesium sulphate and evaporated in vacuum. The oily residue which weighed 8.3 grams was the palmitic acid ester of 2-trifluoromethyl-6-fluoro-9-(3-(4-(2-hydroxyethyl)piperazin-1-yl)-1-propenyl)thioxanthene.

An UV-spectrum showed a maximum extinction $E_{1cm}^{1\%} = 156$ at 278μm. The pharmacological testing of the compounds of the present invention consisted of a standard and reliable, published test showing the neuroleptic activity of the compounds in that they antagonize central nervous stimulating compounds such as amphetamine and methylphenidate. The methylphenidate test was selected after it had proved to be a reliable test method on several known neuroleptics, and reference is made to Pedersen V. & Christensen A.V.: "Methylphenidate antagonism in mice as a rapid screening test for neuroleptic drugs.": Acta pharmacol. et toxicol. 1971, 29, suppl.4, 44.

The test may briefly be described as follows:

As animals were used NMRI male mice weighing 18–25 grams. 5 × 2 mice are used for each dose level.

Thirty minutes, one hour, two hours, three hours etc. after i.p. injection of test substance, methylphenidate, 60 mg/kg, is injected s.c. or p.o. At each time interval separate groups of mice were used. After administration of methylphenidate the mice are placed in the observation cages, 2 in each cage, where they remain for one hour. The cages are placed on corrugated paper, the corrugations facing upwards. It is examined whether or not the mice have been biting the corrugated paper. If not, the substance hashed an antagonistic effect. If one or more of the control pairs have also not been biting the corrugated paper the test has to be repeated on a new set of mice. At each time interval separate groups of mice were used. The peak effect was determined for the test substances and also for a number of known neuroleptics.

The test was carried out on a number of the novel compounds of Formula I and on a number of closely related thiaxanthene derivatives. As reference drugs were used the three known neuroleptics chlorprothixane, chlopenthixol and flupenthixol in the form of the pure alpha-isomers which are the most active isomers, the beta-isomers being inferior in effect.

The following compounds were tested:

2-Trifluormethyl-6-fluoro-9-(3-(4-(2-hydroxyethyl)-piperazine1-yl)-1-propenyl)thioxanthene (called Lu 10-153 for short), 2-Trifluoromethyl-6-fluoro-9-(3-(4-(2-hydroxyethyl-piperidine)-1-propenyl)thioxanthene (called Lu 12-001 for short), 2-Trifluoromethyl-6-fluoro-9-(3-(4-methylpiperazin-1-yl)-1-propenyl) thioxanthene (called Lu 11-185 for short), 2-Trifluoromethyl-6-fluoro-9-(3-dimethylamino-1-propenyl)-thioxanthene (called Lu 11-186 for short), 2-Trifluoromethyl-6-fluoro-9-(3-(4-(2-hydroxyethyl) piperidin1-yl)-1-propenyl) xanthene (called Lu 11-200 for short), 2-Chloro-9-(3-dimethylamino-1-propenyl)-thioxanthene (called Lu 8-030 for short), 2-Chloro-9-(3-(4-(2-hydroxyethyl) piperazin-1-yl)-1-propenyl) thioxanthene (called Lu 9-244 for short), and 2-Trifluoromethyl-9-(3-(4-(2-hydroxyethyl)-piperazine-1-yl)-1-propenyl) thioxanthene (called Lu 9-212 for short).

The results will appear from the following table:

| | Methylphenidate antagonism | | | |
|---|---|---|---|---|
| Substance | peak effect i.p. mg/kg | duration of peak effect/h. | $ED_{50}$ mg/kg 24 h i.p. | Peak effect $ED_{50}$ mg/kg p.c. |
| Lu 10-153 | 0.02 | 30 | 0.06 | 0.03 |
| Lu 12-001 | 0.1 | 72 | 0.1 | 0.2 |
| Lu 11-185 | 0.3 | | | |
| Lu 11-186 | 0.05 | 8 | | 0.08 |
| Lu 11-200 | 0.04 | 17 | 1.6 | 0.2 |
| Lu 8-030 | 3.1 | 3 | >20 | 5.5 |
| Lu 9-244 | 0.3 | 10 | 14.1 | 0.22 |
| Lu 9-212 | 0.11 | 10 | >10 | 0.13 |
| α-chlorprothixen | 2.2 | 2 | >20 | 2.6 |
| α-chlopenthixol | 0.7 | 6 | >20 | 1.3 |
| α-flupenthixol | 0.19 | 6 | >20 | 0.22 |

When comparing the results from the table obviously the compound Lu 10-153 is unique in combining at the same time the most potent peak effect but also the long lasting effect expressed in the duration of peak effect and ED50 24 hours after administration of the substance. When comparing the substances Lu 8-030, Lu 9-244 and Lu 9-212 with the known substances more directly comparable there is a tendency, especially when comparing substances having a trifluoromethyl group at position 2, to a more prolonged activity while the peak effect remains at the same level or is somewhat higher.

The compounds of Formula I and the non-toxic acid addition salts thereof may be administered to animals such as dogs, cats, horses, sheep or the like, including human beings, both orally and parenterally, and may be used for example in the form of tablets, capsules, powders, syrups or in the form of usual sterile solutions for injection. Results upon administration to human beings have been very gratifying.

Most conveniently the compounds of Formula I are administered orally in unit dosage form such as tablets or capsules, each dosage unit containing a non-toxic acid addition salt of one of the said compounds in an amount of from about 0.05 to about 50 mg, most preferably, however, from about 0.5 to 25 mg, calculated as the free amine, the total daily dosage usually ranging from about 0.5 to about 300 mg. The exact individual dosages as well as daily dosages in a particular case will, of course, be determined according to established medical principles under the direction of a physician.

When preparing tablets, the active ingredient is for the most part mixed with ordinary tablet adjuvants such as corn starch, potato starch, talcum, magnesium stearate, gelatine, lactose, gums, or the like.

When the compound of Formula I is an ester, preferably a decanoic acid ester or palmitic acid ester, the composition may advantageously be an oily solution for injection, and such solutions often have a very prolonged effect when compared with the corresponding unesterified compound.

Typical examples of formulas for compositions, containing 2-trifluoromethyl-6-fluoro-9-(3-(4-(2-hydroxyethyl)piperazine-1-yl)-1-propenyl) thioxanthene (called Lu 10-153 for short) as the active ingredient, are as follows:

| 1) | Tablets containing 1 milligram of Lu 10-153 calculated as the free base in the form of the dihydrochloride: | |
|---|---|---|
| | Lu 10-153 | 1 mg |
| | lactose 37 | mg |
| | potato starch | 74 mg |
| | gelatine | 2 mg |
| | talcum | 8 mg |
| 2) | Solution for injection containing per ml: | |
| | Lu 10-153 | 0.5 mg |
| | sodium chloride | 9.0 mg |
| | sterile water ad | 1 ml |
| 3) | Syrup containing per milliliter: | |
| | Lu 10-153 | 0.2 mg |
| | methyl-paraben | 1.0 mg |
| | propyl-paraben | 0.1 mg |
| | saccharose | 400 mg |
| | water ad | 1 ml |
| 4) | Capsules containing per capsule: | |
| | Lu 10-153 | 2 mg |
| | lactose | 40 mg |
| | magnesium stearate | 0.5 mg |

Any other pharmaceutical tableting adjuvants may be used provided that they are compatible with the active ingredient, and additional compositions and dosage forms may be similar to those presently used for neuroleptics such as thiothixene, clopenthixol or flupenthixol. Also combination of the compounds of Formula I as well as their non-toxic acid salts with other active ingredients, especially other neuroleptics, thymoleptics, tranquilizers or the like, fall within the scope of the present invention.

As previously stated, when isolating the compounds of Formula I in the form of an acid addition salt, the acid is preferably selected so as to contain an anion which is non-toxic and pharmacologically acceptable, at least in usual therapeutic doses. Representative salts which are included in this preferred group are the hydrochlorides, hydrobromides, sulphates, acetates, phosphates, nitrates, methanesulphonates, ethanesulphonates, lactates, citrates, tartrates or bitartrates, embonates and maleates of the amines of Formuls I. Other acids are likewise suitable and may be employed if desired. For example: Fumaric, benzoic, ascorbic, succinic, salicylic, bismethylenesalicylic, propionic, gluconic, malic, malonic, madelic, cinnamic, citraconic, stearic, palmitic, itaconic, glycolic, benzenesulphonic, and sulphamic acids may also be employed as acid addition saltforming acids.

When desired to isolate a compound of the invention in the form of the free base, this may be done according to conventional procedure as by dissolving the isolated or unisolated salt in water, treating with a suitable alkaline material, extracting the liberated free base with a suitable organic solvent drying the extract and evaporating to dryness.

The invention also comprises a method for the alleviation, palliation mitigation or inhibition of the manifestations of certain physiological-psychological abnormalies of animals by administering to a living animal body, including human beings, an adequate quantity of a compound of Formula I or a non-toxic acid addition salt thereof. An adequate quantity would be from about 0.001 mg to about 1 mg per Kg of body weight in each unit dosage and from about 0.003 milligrams to about 3 milligrams/kg of body weight per day.

It is to be understood that the invention is not limited to the exact details of operation or exact compound or compositions shown and described, as obvious modifications and equivalents will be apparent to one skilled in the art.

We claim:
1. A pharmaceutical composition, useful as a tranquilizer or neuroleptic and for the treatment of psychoses, in unit dosage form, comprising a major quantity of a pharmaceutical carrier and as an active ingredient a pharmaceutically effective dose of a compound selected from the group consisting of 1) a compound of the following formula:

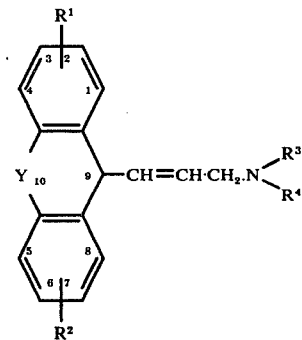

wherein Y is selected from the group consisting of sulphur and oxygen, $R^1$ is selected from the group consisting of hydrogen, chlorine, trifluoromethyl and dimethylsulfamoyl, $R^2$ is selected from the group consisting of hydrogen and fluorine, and $R^3$ and $R^4$ taken together with the nitrogen atom form a ring selected from the group consisting of a piperazine and a piperidine ring, such rings substituted in the 4-position by a substituent selected from a methyl group, a 2-hydroxyethyl group, and a 2-hydroxyethyl group esterified with an aliphatic carboxylic acid having from one to seventeen carbon atoms inclusive, and 2) a non-toxic acid addition salt thereof.

2. A composition according to claim 1, wherein the active ingredient is present in an amount of from 0.05 to 50 milligrams per unit dose calculated as the free amine.

3. A composition according to claim 1, wherein the active ingredient is present in an amount of from 0.5 to 25 milligrams per unit dose calculated as the free amine.

4. A composition according to claim 1, wherein the active ingredient is selected from the group consisting of 2-trifluoromethyl-6-fluoro-9-(3-(4-(2-hydroxyethyl)piperazin1-yl)-1-propenyl)thioxanthene and a non-toxic acid addition salt thereof.

5. A composition according to claim 1, wherein the active ingredient is selected from the group consisting of 2-trifluoromethyl-6-fluoro-9-(3-(4-(2-hydroxyethyl)piperidine) 1-propenyl)thioxanthene and a non-toxic addition salt thereof.

6. A composition according to claim 3, wherein the active ingredient is selected from the group consisting of 2-trifluoromethyl-6-fluoro-9-(3-(4-(2-hydroxyethyl)piperazin1-yl)-1-propenyl)thioxanthene and a non-toxic acid addition salt thereof.

7. A composition according to claim 3, wherein the active ingredient is selected from the group consisting of 2-trifluoromethyl-6-fluoro-9-(3-(4-(2-hydroxyethyl)piperidine) 1-propenyl)thioxanthene and a non-toxic addition salt thereof.

8. Method of treating a living animal body in need of tranquilization or treatment for psychoses, comprising the step of administering to the said living animal body an effective tranquilizing or neuroleptic amount of a compound selected from the group consisting of 1) a compound of the following formula:

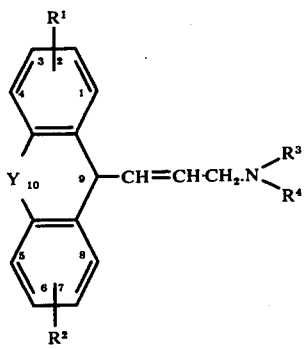

I wherein Y is selected from the group consisting of sulphur and oxygen, $R^1$ is selected from the group consisting of hydrogen, chlorine, trifluoromethyl and dimethylsulfamoyl, $R^2$ is selected from the group consisting of hydrogen and fluorine, and $R^3$ and $R^4$ taken together with the nitrogen atom form a ring selected from the group consisting of a piperazine and a piperidine ring, such rings substituted in the 4-position by a substitutent selected from a methyl group, a 2-hydroxyethyl group, and a 2-hydroxyethyl group esterified with an aliphatic carboxylic acid having from one to seventeen carbon atoms inclusive, and 2) a non-toxic acid addition salt thereof.

9. Method according to claim 8, wherein the compound is administered in an amount of 0.05 to 50 milligrams per unit dose calculated as the free amine.

10. Method according to claim 8, wherein the compound is administered in an amount of 0.5 to 25 milligrams per unit dose calculated as the free amine.

11. Method according to claim 8, wherein the compound is selected from the group consisting of 2-trifluoromethyl-6-fluoro-9-(3-(4-(2-hydroxyethyl)piperaZin-1-yl)-1-propenyl)-thioxanthene and a non-toxic acid addition salt thereof.

12. Method according to claim 8, wherein the compound is selected from the group consisting of 2-trifluoromethyl-6fluoro-9-(3-(4-(2-hydroxyethyl)-piperidine)1-propenyl)thioxanthene and a non-toxic addition salt thereof.

13. Method according to claim 8, wherein the compound is administered in a total daily dosage of 0.5 to about 300 mg.

14. Method according to claim 8, wherein the amount of compound administered is 0.001 mg. to about 1 m. per Kg. of body weight per unit dosage.

15. Method according to claim 8, wherein the amount of compound administered is 0.003 mg. to about 3 mg. per kg. of body weight per day.

* * * * *

UNITED STATES PATENT OFFICE
CERTIFICATE OF CORRECTION

Patent No. 4,022,896　　　　　　　　　Dated May 10, 1977

Inventor(s) Georg Ujvari, Peter Bregnedal Hansen

It is certified that error appears in the above-identified patent and that said Letters Patent are hereby corrected as shown below:

Col. 4, line 5: "trifluoromethyl6" should read ---trifluoromethyl-6---
Col. 4, line 18: "2propanol" should read ---2-propanol---
Col. 4, line 61: "2allylidene" should read ---2-allylidene---
Col. 4, line 66: "dded" should read ---added---
Col. 6, line 21: "chloro9" should read ---chloro-9---
Col. 6, line 33: "chloro9" should read ---chloro-9---

Col. 8, line 14: "piperazinel-yl" should read ---piperazine-1-yl---
Col. 8, line 26: "piperidinl-yl" should read ---piperidin-1-yl---
Col. 8, line 42: "p.c." should read ---p.o.---
Col. 9, line 38: "lactose37 mg" should read ---lactose 37mg---
Col. 9, line 49: "water ad 1 ml" should read ---water ad 1 ml---
Col. 10, line 6: "Formuls" should read ---Formula---
Col. 11, line 16: "piperazinl-yl" should read ---piperazin-1-yl---
Col. 11, line 26: "piperazinl-yl" should read ---piperazin-1-yl---
Col. 12, line 31: "piperaZin" should read ---piperazin---
Col. 12, line 35: "6fluoro" should read ---6-fluoro---

Signed and Sealed this

Second Day of May 1978

[SEAL]

Attest:

RUTH C. MASON　　　　　　LUTRELLE F. PARKER
Attesting Officer　　　Acting Commissioner of Patents and Trademarks